US009451734B2

(12) United States Patent
Onuma et al.

(10) Patent No.: US 9,451,734 B2
(45) Date of Patent: Sep. 20, 2016

(54) MAGNETIC SHIELDING DEVICE AND MAGNETIC SHIELDING METHOD

(71) Applicant: Seiko Epson Corporation, Tokyo (JP)

(72) Inventors: Fumihiko Onuma, Hino (JP); Shigemitsu Toda, Zama (JP); Ryuji Hokari, Tokyo-to (JP)

(73) Assignee: Seiko Epson Corporation (JP)

( * ) Notice: Subject to any disclaimer, the term of this patent is extended or adjusted under 35 U.S.C. 154(b) by 451 days.

(21) Appl. No.: 14/029,001

(22) Filed: Sep. 17, 2013

(65) Prior Publication Data

US 2014/0077612 A1    Mar. 20, 2014

(30) Foreign Application Priority Data

Sep. 18, 2012 (JP) ................. 2012-204462
Sep. 11, 2013 (JP) ................. 2013-188097

(51) Int. Cl.
| | | |
|---|---|---|
| H04B 3/00 | (2006.01) |
| H05K 9/00 | (2006.01) |
| G01R 33/022 | (2006.01) |
| G01R 33/00 | (2006.01) |
| G01R 33/025 | (2006.01) |
| A61B 5/04 | (2006.01) |

(52) U.S. Cl.
CPC ......... H05K 9/0071 (2013.01); G01R 33/0076 (2013.01); G01R 33/022 (2013.01); G01R 33/025 (2013.01); A61B 5/04007 (2013.01); A61B 5/04008 (2013.01); A61B 2562/18 (2013.01)

(58) Field of Classification Search
CPC ............ H05K 9/0071; G01R 33/0076; G01R 33/022; G01R 33/025
See application file for complete search history.

(56) References Cited

U.S. PATENT DOCUMENTS

| | | | | |
|---|---|---|---|---|
| 5,187,327 A | * | 2/1993 | Ohta | ............... H05K 9/0077 174/15.4 |
| 7,193,413 B2 | | 3/2007 | Kandori et al. | |
| 2014/0077612 A1 | | 3/2014 | Onuma et al. | |

FOREIGN PATENT DOCUMENTS

| | | |
|---|---|---|
| JP | 06-167583 | 6/1994 |
| JP | 2002-094280 A | 3/2002 |
| JP | 2002-257914 A | 9/2002 |
| JP | 2003-167038 A | 6/2003 |
| JP | 2003167038 A * | 6/2003 |
| JP | 2003-243874 A | 8/2003 |
| JP | 2003-273565 A | 9/2003 |
| JP | 2005-016960 A | 1/2005 |
| JP | 2005-294537 A | 10/2005 |
| JP | 2007-129049 A | 5/2007 |
| JP | 2008-282983 A | 11/2008 |
| JP | 2009-175067 A | 8/2009 |
| JP | 2009-229325 A | 10/2009 |
| JP | 4377566 B2 | 12/2009 |
| JP | 2010-093242 A | 4/2010 |
| JP | 2011-082444 A | 4/2011 |
| JP | 2014-060270 A | 4/2014 |

* cited by examiner

*Primary Examiner* — Daniel Cavallari
(74) *Attorney, Agent, or Firm* — Harness, Dickey & Pierce, P.L.C.

(57) ABSTRACT

A magnetic shielding device includes: a passive shield having an inner space; a first coil that cancels a magnetic field entering in the inner space; a first magnetic sensor that measures the magnetic field entering in the inner space; a second magnetic sensor located in a position farther from the first coil than the first magnetic sensor; and a controller that controls the first coil so that a gradient between a first magnetic field measured by the first magnetic sensor and a second magnetic field measured by the second magnetic sensor be less than a predetermined threshold.

9 Claims, 9 Drawing Sheets

MAGNETIC SHIELDING DEVICE AND MAGNETIC SHIELDING METHOD

CROSS REFERENCE TO RELATED APPLICATIONS

The entire disclosures of Japanese Patent Applications No. 2013-188097 filed on Sep. 11, 2013, and No. 2012-204462 filed on Sep. 18, 2012 are expressly incorporated by reference herein.

BACKGROUND

1. Field

The invention relates to magnetic shielding device and magnetic shielding method.

2. Related Art

Diagnostic imaging is widely used in medical procedures. Since the diagnostic imaging is a non-invasive procedure, the diagnostic imaging is preferably used for a sensitive organ such as a heart or a brain. Magnetic field source imaging is one example of the diagnostic imaging. These organs generate current caused by activities of neuron. Measurement of the magnetic field caused by the current reflects status of these organs. For example, Magnetocardiogram (MCG), measurement of the magnetic filed generated by a heart, and Magnetoencephalogram (MEG), measurement of the magnetic field generated by a brain, are known.

There are two major problems for measuring these magnetic fields. The first problem relates to a sensitivity of a measuring device. To measure these magnetic fields, a high sensitivity is required. The second problem relates to an external magnetic field. Since an external magnetic field caused by the earth magnetism, for example, is hundred thousands times greater than a magnetic field generated by a living body, a magnetic shielding device to shield the external magnetic field is required.

SUMMARY

The invention provides a magnetic shielding device and a magnetic shielding method for reducing a gradient of a magnetic field of an inner space of a magnetic shield.

According to one aspect of the invention, there is provided a magnetic shielding device, including: a passive shield having an inner space; a first coil that cancels a magnetic field entering in the inner space; a first magnetic sensor that measures the magnetic field entering in the inner space; a second magnetic sensor located in a position farther from the first coil than the first magnetic sensor; and a controller that controls the first coil so that a gradient between a first magnetic field measured by the first magnetic sensor and a second magnetic field measured by the second magnetic sensor be less than a predetermined threshold.

The passive shield may have at least one opening.

The second magnetic shield may be located nearer a target space compared with the first magnetic sensor in a measurement direction of a magnetic field measuring device installed in the target space, the target space being a part of the inner space.

The threshold may be determined based on a range of a magnetic field used in a device installed in a target space, the target space being a part of the inner space.

The threshold may cause difference in a magnetic field between edges of a target space to be less than 10 nT, the target space being a part of the inner space.

The magnetic shielding device may further include a second coil that cancels a magnetic field in a target space, the target space being a part of the inner space.

The magnetic shielding device may further include a first driver circuit that drives the first coil; and a second driver circuit that drives the second coil.

The passive shield may have at least one opening, and the first driver circuit may provide current causing the first coil to cancel a magnetic field at an edge face of the opening.

The first magnetic sensor may be located at the edge face, and the first driver circuit may provide current that cancels a magnetic field measured by the first magnetic sensor.

The first magnetic sensor may be located at the center of the edge face.

The second driver circuit may provide current causing the second coil to cancel a magnetic field in the inner space.

The second magnetic sensor may be located in the inner space, and the second driver circuit may provide current causing the second coil to cancel a magnetic field measured by the second magnetic sensor.

A dynamic range of a magnetic field generated by the first coil may be greater than a dynamic range of a magnetic field generated by the second coil.

A resolution in a magnetic field generated by the second coil may be higher than a resolution of a magnetic field generated by the first coil.

The passive shield may includes two openings, the magnetic shielding device may include two first coils, and each of the two first coils may cancel a magnetic field near one of the two openings, respectively.

The first driver circuit may provide current having the same magnitude to the two first coils.

According to another aspect of the invention, there is provided a method in magnetic shielding device including a passive shield having an inner space, a first coil that cancels a magnetic field entering in the inner space, a first magnetic sensor that measures the magnetic field entering in the inner space, a second magnetic sensor located in a position farther from the first coil than the first magnetic sensor, the method including: controlling the first coil so that a gradient between a first magnetic field measured by the first magnetic sensor and a second magnetic field measured by the second magnetic sensor be less than a predetermined threshold.

BRIEF DESCRIPTION OF THE DRAWINGS

Embodiments of the invention will be described in detail based on the following figures, wherein.

DESCRIPTION OF EXEMPLARY EMBODIMENTS

First Exemplary Embodiment

Configuration

Figure 1:
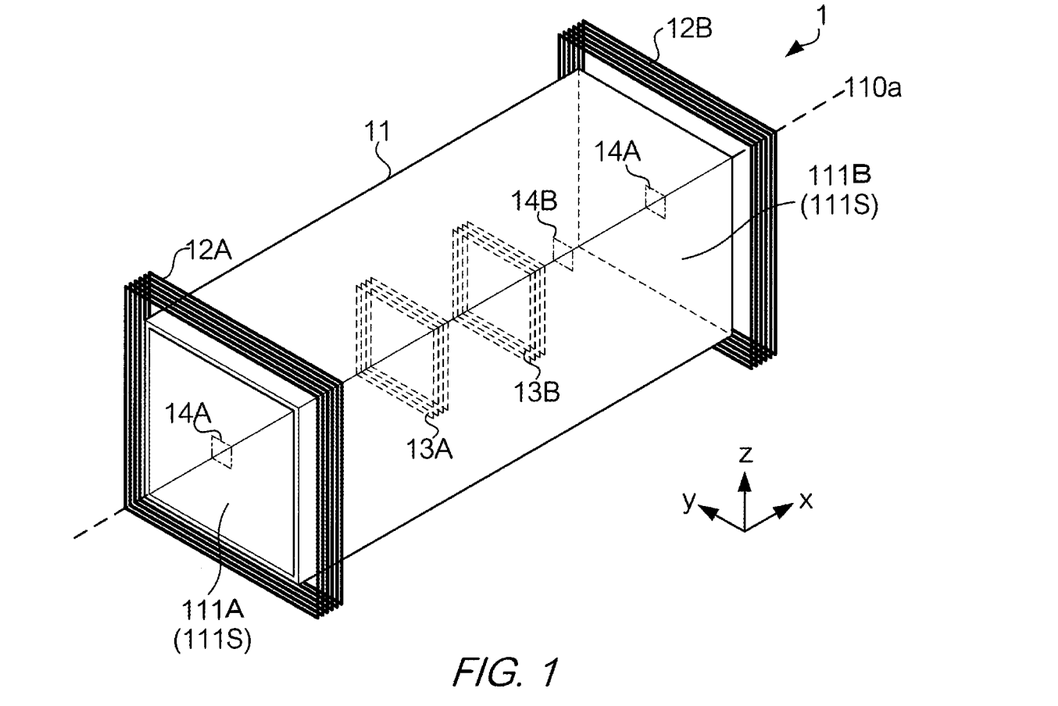
FIG. 1 shows an example of an external view of magnetic shielding device 1 according a first exemplary embodiment.

FIG. 1 shows an example of an external view of magnetic shielding device 1 according a first exemplary embodiment. Magnetic shielding device 1 is used to shield a device such as a magnetic measuring device from an external magnetic field, which is a magnetic field caused by an object other than an object to be measured. Magnetic shielding device 1 includes passive shield 11, external coil 12, internal coil 13, and magnetic sensor 14.

Passive shield 11 is made of conductive material having a high conductivity such as Aluminum. Such material shields a magnetic field by eddy current.

Passive shield 11 may be made of ferromagnetic substance, such as permalloy, ferrite, or amorphous of iron, chromium, or cobalt. Passive shield 11 has tubular shape whose cross section has square shape. A term "inner space" refers to a space surrounded by passive shield 11 and a term "outer space" refers to a space other than the inner space. The inner space is so large that the inner space can accommodate a magnetic field measuring device (for example, a magnetocardiographic device) and a tested body (for example, a person). Among the inner space, a space where magnetic field is a target to be cancelled, is referred to as a "target space" (not shown in FIG. 1). In magnetic shielding device 1, a magnetic field measuring device is installed and used at the target space.

For the description below, a three dimensional orthogonal coordinate system is defined. In the coordinate system, x-axis, y-axis, and z-axis are defined as a direction along the width direction, the depth direction, and the height direction of passive shield 11, respectively. In this example, passive shield 11 has two openings, opening 111A and opening 111B.

External coil 12A and external coil 12B are coils to cancel a magnetic field entering the inner space of passive shield 11. External coil 12A and external coil 12B are located near opening 111A and opening 111B in the outer space, respectively.

Magnetic sensor 14A is a sensor to measure a magnetic field entering the inner space. In this example, magnetic sensor 14 is located at the center of opening 111A. Further, magnetic sensor 14A is used to measure a gradient of the magnetic field as described above.

Figure 2:
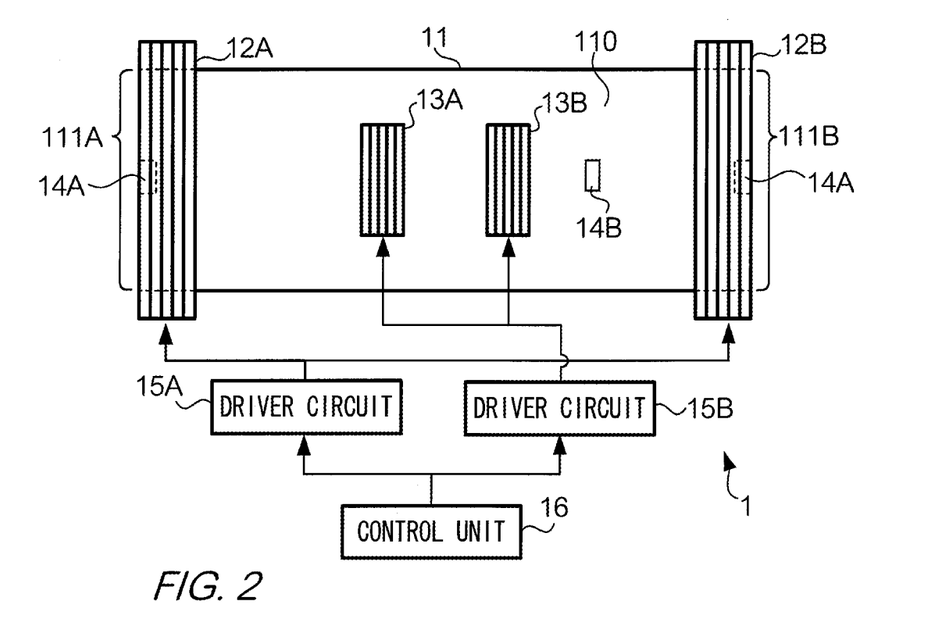
FIG. 2 shows an example of a configuration of magnetic shielding device 1.

FIG. 2 shows an example of a configuration of magnetic shielding device 1. In the figure, driver circuit 15 and control unit 16 are shown in addition to a schematic of a cross section along y-axis. Internal coil 13A and internal coil 13B are coils to cancel a magnetic field in the target space. In the example, external coil 12 and internal coil 13 are Helmholtz coils. In other words, internal coil 13 provides spatially homogeneous magnetic field so as to control an offset of the magnetic field in the target space.

Magnetic sensor 14B is a sensor to measure a magnetic field in the inner space. Magnetic sensor 14B is located at a position nearer the target space (more specifically, the center of the target space), compared with magnetic sensor 14A. In this example, magnetic sensor 14B is located outside the target space. More specifically, magnetic sensor 14B is located at a position nearer the target space in a measurement direction (for example, x-axis) of the magnetic field measuring device installed in the target space, compared with magnetic sensor 14A. It is to be noted that magnetic sensor 14A is located at a position nearer external coil 12, compared with magnetic sensor 14B.

Driver circuit 15A is a circuit to drive external coil 12. Driver circuit 15B is a circuit to drive internal coil 13. Control unit 16 controls driver circuits 15A and 15B, in response to a magnetic field measured by magnetic sensor 14. More specifically, control unit 16 controls driver circuit 15A (in other words, external coil 12) so that a gradient (or difference) between a magnetic field measured by magnetic sensor 14A and a magnetic field measured by magnetic sensor 14B is less than a predetermined threshold. The threshold may be stored in a memory of magnetic shielding device 1 in advance, or may be input by a user.

2. Operation

Figure 3:
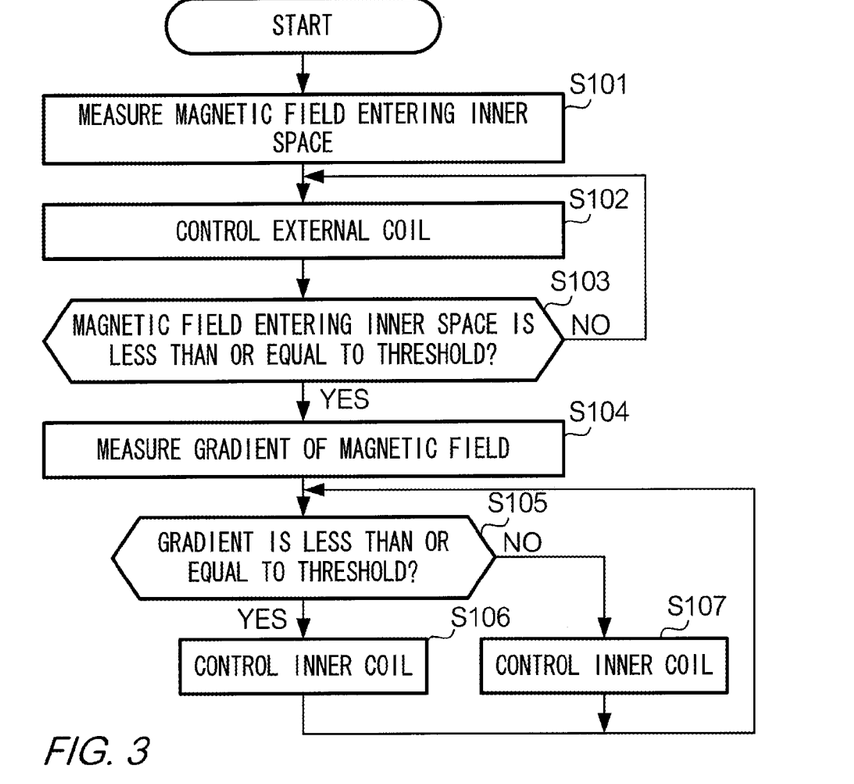
FIG. 3 shows an example of a flowchart illustrating an operation of magnetic shielding device 1.

FIG. 3 shows an example of a flowchart illustrating an operation of magnetic shielding device 1. The operation shown in FIG. 3 is triggered by activating magnetic shielding device, for example.

In step S101, magnetic shielding device 1 measures a magnetic field near the opening of passive shield 11. More specifically, control unit 16 obtains a signal showing results of measurement of the magnetic field, from magnetic sensor 14A.

In step S102, control unit 16 controls the coils so that the magnetic field near the opening is less than a predetermined threshold. More specifically, control unit 16 outputs to driver circuit 15A a signal to provide external coil 12 current for canceling the magnetic field measured by magnetic sensor 14A. Driver circuit 15A provides current to external coil 12 in accordance with the signal output from control unit 16. The current provided to external coil 12 generates a magnetic field having a direction opposite to a direction of the magnetic field measured by magnetic sensor 14A. The current provided to external coil 12 has a magnitude to generate a magnetic field having the same magnitude as the magnetic field measured by magnetic sensor 14A. The relationship between the magnitude of current and the magnitude of a magnetic field is stores in a ROM (Read Only Memory) of control unit 16.

In this example, control unit 16 also controls internal coil 13. For example, control unit 16 outputs a signal causing driver circuit 15B to provide current so as to cancel the magnetic field measured by magnetic sensor 14B.

In step S103, control unit determines whether the magnitude of a magnetic field near the opening is less than or equal to a predetermined threshold (for example, 10 nT (nano tesla)). More specifically, control unit 16 obtains a signal showing the measured magnetic field from magnetic sensor 14A. Control unit 16 determines whether the magnitude of a magnetic field shown by the signal is less than or equal to the threshold, If it is determined that the magnitude of the magnetic field is greater than the threshold (step S103:

YES), control unit 16 transfers the operation to step S102, If it is determined that the magnitude of the magnetic field is less than or equal to the threshold (step S103: NO), control unit 16 transfers the operation to step S104.

In step S104, control unit 16 measures a gradient of a magnetic filed in the inner space. More specifically, control unit 16 obtains a signal showing the measured magnetic field of the inner space from magnetic sensor 14B. Control unit 16 calculates the gradient of a magnetic filed between magnetic sensors 14A and 14B, using the magnetic filed measured by magnetic sensor 14A, the magnetic field measured by magnetic sensor 14B, and a distance between magnetic sensors 14A and 14B. The distance between magnetic sensors 14A and 14B is stored in the ROM of control unit 16. Alternatively, the distance between magnetic sensors 14A and 14B may be measured and input by a user.

In step S105, control unit 16 determines the gradient in the inner space is less than or equal to a predetermined threshold. If it is determined that the gradient in the inner space is less than or equal to the threshold (step S105: YES), control unit 16 transfers the operation to step S106. If it is determined that the gradient in the inner space is greater than the threshold (step S105: NO), control unit 16 transfers the operation to step S107.

It is to be noted that the threshold of the gradient used in step S105 is determined, for example, according to a use range (for example, a dynamic range of a measurement in a magnetic field measuring device) of a device (for example, a magnetic field measuring device). More specifically, the threshold is determined so that the difference in the magnetic field between edges of the target space is less than a predetermined value (for example, 10 nT) corresponding to a dynamic range of a magnetic field measuring device. For example, in a case that the dynamic range of the magnetic field measuring device is 10 nT, the threshold is determined so that the difference, which is equal to a product of the gradient and the length in a direction of x-axis, in the magnetic field between edges of the target space in x-axis is less than the dynamic range. For more detailed example, if the target space has 1 m length in x-axis direction, the threshold is determined as 10 nT/m. It is to be noted that the threshold of the magnetic field may be less than 10 nT, for example, 3 nT.

In step S106, control unit 16 maintain current provided to external coil 12 and internal coil 13. Control unit 16 transfers the operation to step S103.

In step S107, control unit 16 controls at least one of external coil 12 and internal coil 13 so that the magnitude of the gradient of the magnetic field decrease. In this process, control unit 16 controls a gradient of a magnetic field in the target space, with the magnitude of the magnetic field in the target space being less than or equal to a predetermined threshold (for example, 10 nT. Note that the threshold may be different from the threshold used in step S103). In this example, since magnetic sensor 14B is outside the target space, magnetic sensor 14B cannot directly measures the magnetic field in the target space. Therefore, control unit 16 estimates a magnetic field in the inner space. Control unit 16 controls at least one of external coil 12 and internal coil 13 so that the estimated magnitude of the magnetic field in the inner space is less than or equal to a threshold, and the gradient of the magnetic field in the inner space is less than or equal to a threshold.

Any algorithm can be used for estimating a magnetic field in the inner space. For example, if the magnetic field measured by magnetic sensor 14B is greater than the magnetic field measured by magnetic sensor 14A, control unit 16 controls current provided to external coil 12 so that the magnetic field generated by external coil 12 increases. If the magnetic field measured by magnetic sensor 14B is less than the magnetic field measured by magnetic sensor 14A, control unit 16 controls current provided to external coil 12 so that the magnetic field generated by external coil 12 decreases. After controlling the current, control unit 16 estimates the magnetic field in the target space. The magnetic field in the target space is estimated using results of measurements by magnetic sensors 14A and 14B, and the distance between magnetic sensors 14A and 14B. If the estimated magnitude of the magnetic field is greater than the threshold, control unit 16 controls current provided to internal coil 13 so that the magnetic field in the inner space is reduced (in other words, offset of the magnetic field in controlled).

After the control, control unit 16 transfers the operation to step S102. It is to be noted that the current provided to internal coil 13 may be controlled in addition to or instead of the control of external coil 12 in step S107.

Figure 4:
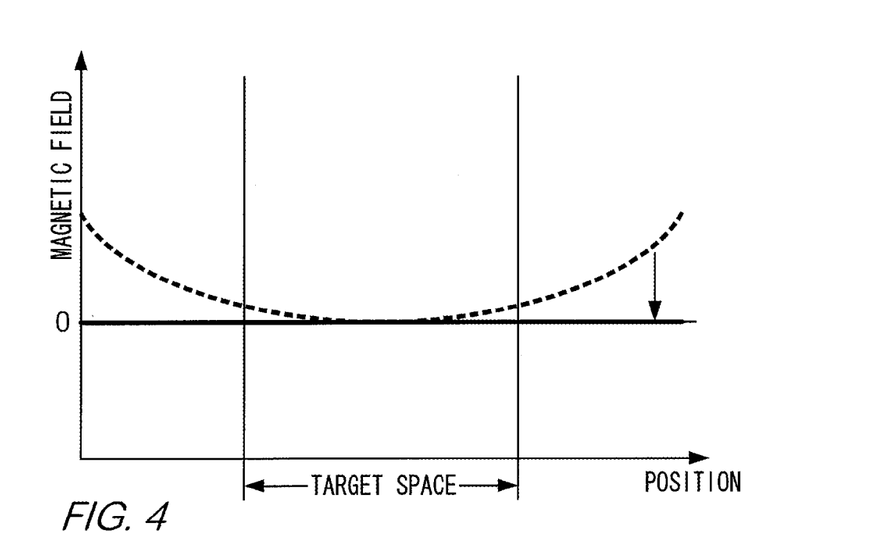
FIG. 4 shows an example of a decreased gradient of the magnetic field.

FIG. 4 shows an example of a decreased gradient of the magnetic field. The vertical axis and the horizontal axis show the magnetic field and spatial position, respectively. The dashed line shows a profile without decreasing the gradient, and the solid line shows a profile with decreasing the gradient. According to the operation shown in FIG. 3, the magnetic field entering the inner space is reduced less than a threshold, and the gradient of the magnetic field of the inner space is reduced less than a threshold. In other words, magnet shielding device 1 can provide an inner space where the gradient of the magnetic field is reduced.

3. Examples of Configuration of Magnetic Sensors

The spatial configuration (or layout) of the magnetic sensors are not restricted to an example shown in FIG. 2. Other examples will be described in the following. In FIGS. 5 to 9, target space 112 is shown in the figures. Internal coil 13 and driver circuit 15B is not shown in the following figures.

Figure 5:
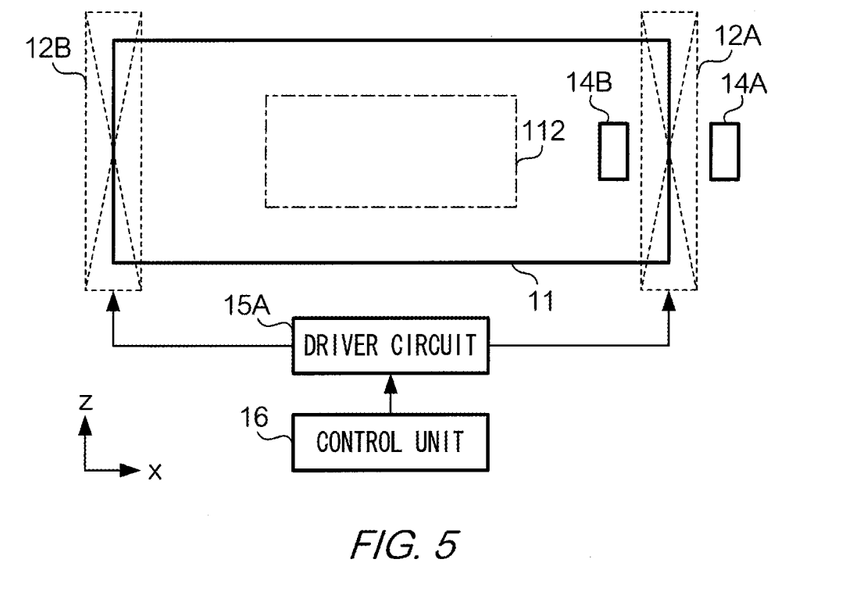
FIG. 5 shows an example of a configuration of magnetic sensors.

FIG. 5 shows an example of a configuration of magnetic sensors. In this example, magnetic sensor 14A is located not in the inner space but out of the passive shield (in the outer space). It is to be noted that magnetic sensor 14B may be located outside target space 112.

Figure 6:
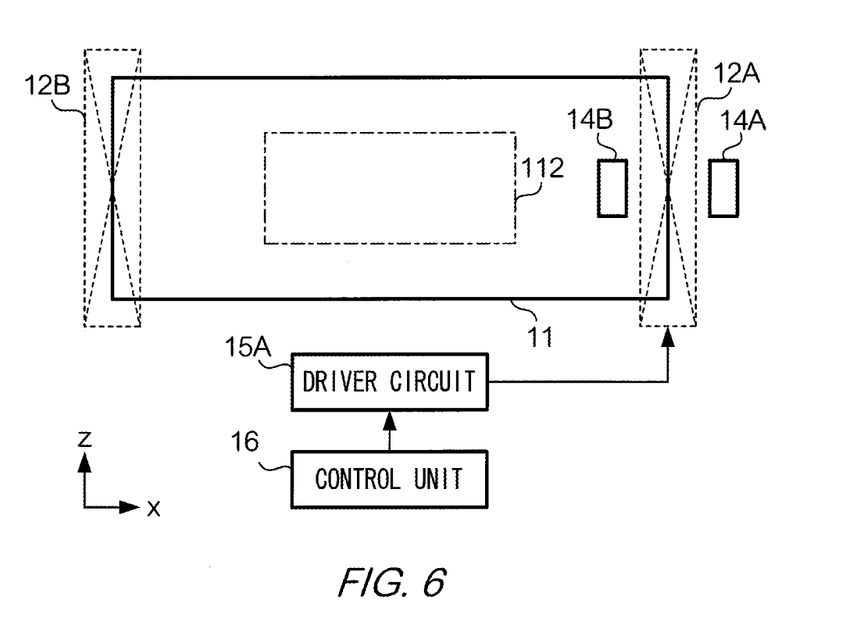
FIG. 6 shows another example of a configuration of magnetic sensors.

FIG. 6 shows another example of a configuration of magnetic sensors. In this example, a single external coil (external coil 12B) is driven. External coil 12A is not driven.

Figure 7:
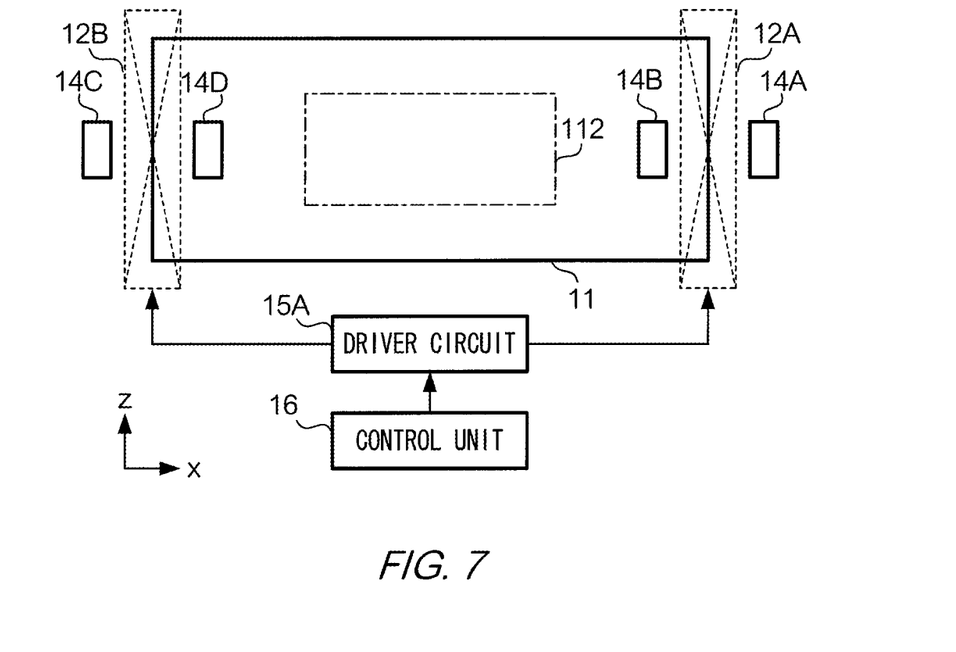
FIG. 7 shows still another example of a configuration of magnetic sensors.

FIG. 7 shows yet another example of a configuration of magnetic sensors. In this example, two sets of sensors are used. The first set of sensors measure the magnetic field entering the inner space. The second set of sensors measure the magnetic field of the inner space. Magnetic sensors 14A and 14C measure the magnetic field entering the inner space. In this example, passive shield 11 has two openings. Magnetic sensor 14A measures a magnetic field near the first opening and magnetic sensor 14B measures a magnetic field near the second opening. Magnetic sensors 14B and 14D measure the magnetic field of the inner space. Magnetic sensor 14B is located nearer magnetic sensor 14A, compared with magnetic sensor 14D. Magnetic sensor 14D is located nearer magnetic sensor 14B, compared with magnetic sensor 14A. In this example, the gradient of the magnetic field between magnetic sensors 14A and 14B and the gradient of the magnetic field between magnetic sensors 14C and 14D, are controlled so as to be less than a predetermined threshold, respectively.

Figure 8:
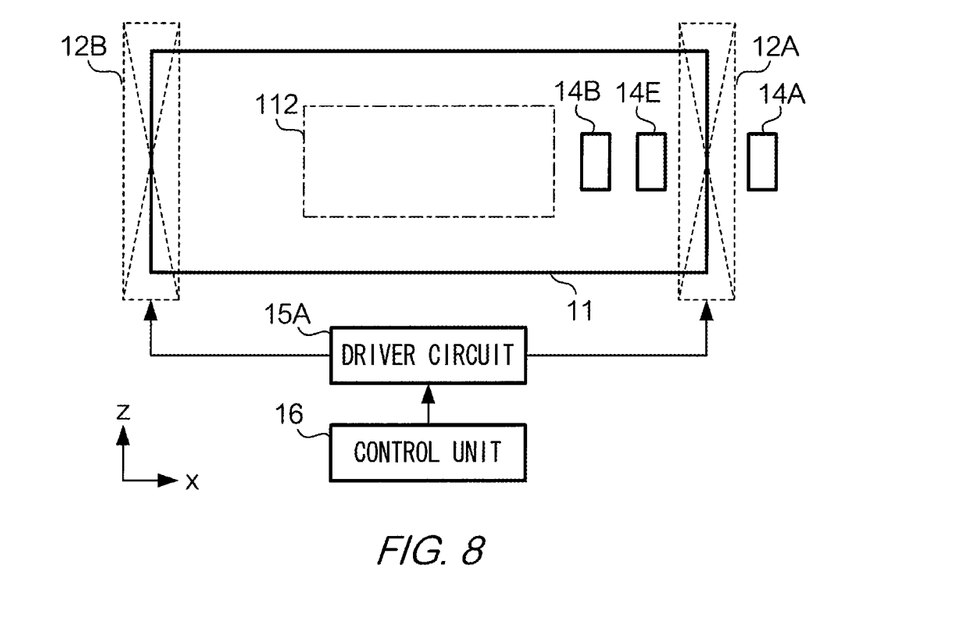
FIG. 8 shows still another example of a configuration of magnetic sensors.

FIG. 8 shows yet another example of a configuration of magnetic sensors. In this example, three magnetic sensors are used to measure the gradient of the magnetic field. Magnetic field 14A measures the magnetic field entering the inner space. Magnetic sensors 14B and 14E measure the magnetic field of the inner space. Magnetic sensors 14B and 14E are located at different position each other. In this example, the gradient of the magnetic field is determined using three items of data measured by three sensors and a predetermined algorithm (for example, least square algorithm). It is to be noted that four or more magnetic sensors may be used to determine the gradient of the magnetic field.

In another example of FIG. 8, magnetic sensor 14A may not be used to determine the gradient of the magnetic field. In other words, magnetic sensor 14A may be used only for controlling external coil 12A (or measuring the magnetic field entering the inner space). In such a case, the gradient of the magnetic field is determined by magnetic sensors 14B and 14C.

Figure 9:
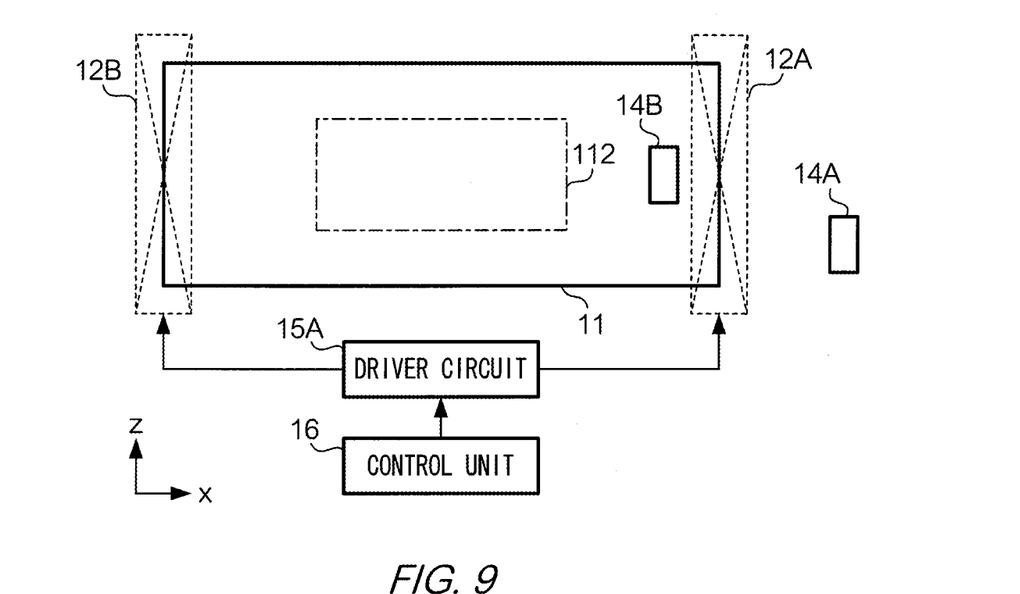
FIG. 9 shows still another example of a configuration of magnetic sensors.

FIG. 9 shows yet another example of a configuration of magnetic sensors. In this example, magnetic sensor 14A is located at a position outside passive shield 11. Since magnetic sensor 14A is used to estimate the magnetic field entering the inner space, magnetic sensor 14A may be located far from the opening, not close to the opening.

In the above examples, magnetic sensor 14B is located outside the target space. However, magnetic sensor 14B may be located in the target space. Further, magnetic sensor 14B may not be located near the target space. In a case that a magnetic sensor is located in the target space, the magnetic sensor should have higher sensitivity than the second magnetic sensor measuring the magnetic field entering the inner space, so that the magnetic field measured by the magnetic sensor is less than a threshold. However, in the present embodiment, two magnetic sensors may be located near the opening and the sensitivities of these two sensors may be the same level. Further, in a case that a magnetic sensor is located outside the target space, the target space can be used effectively.

4. Modification

The invention is not restricted to the embodiment described above. Various modifications may be applied to the embodiment. Some modifications will be described in the following. Two or more modification may be combined.

The shape of passive shield 11 is not restricted to the example described in the embodiment above. For example, the number of openings and the shape of the openings are not restricted to the example described above. Passive shield 11 may not have an opening, or may have s single opening. Alternatively, an opening may be covered by a cover.

The cross section perpendicular to x-axis is not restricted to a square. For example, the cross section perpendicular to x-axis may be a polygon other than a square, a circle, or an ellipse. Further, passive shield 11 may be made of multi-layered material.

Internal coil 13 may be omitted. In a case that magnetic shielding device 1 does not have internal coil 13, the gradient of the magnetic shield is controlled by current provided to external coil 12. Further, the shape of external coil 12 and internal coil 13 are not restricted to the example described above. The shape of these coils may be a polygon other than a square, a circle, or an ellipse.

In the above embodiment, only an x-axis component of the magnetic field is cancelled. However, two or more axes components may be cancelled or controlled. In such a case, magnetic shielding device 1 has two or more sets of internal coils 13. For example, magnetic shielding device 1 may have three sets of internal coils 13, for x-, y-, and z-axes. Each component of the magnetic field may be cancelled or controlled.

A method for controlling a coil is not restricted to the example described above. In the above embodiment, each coil is feedback controlled. A coil may be controlled by a method other than the feedback control.

B. Second Exemplary Embodiment

Figure 10:
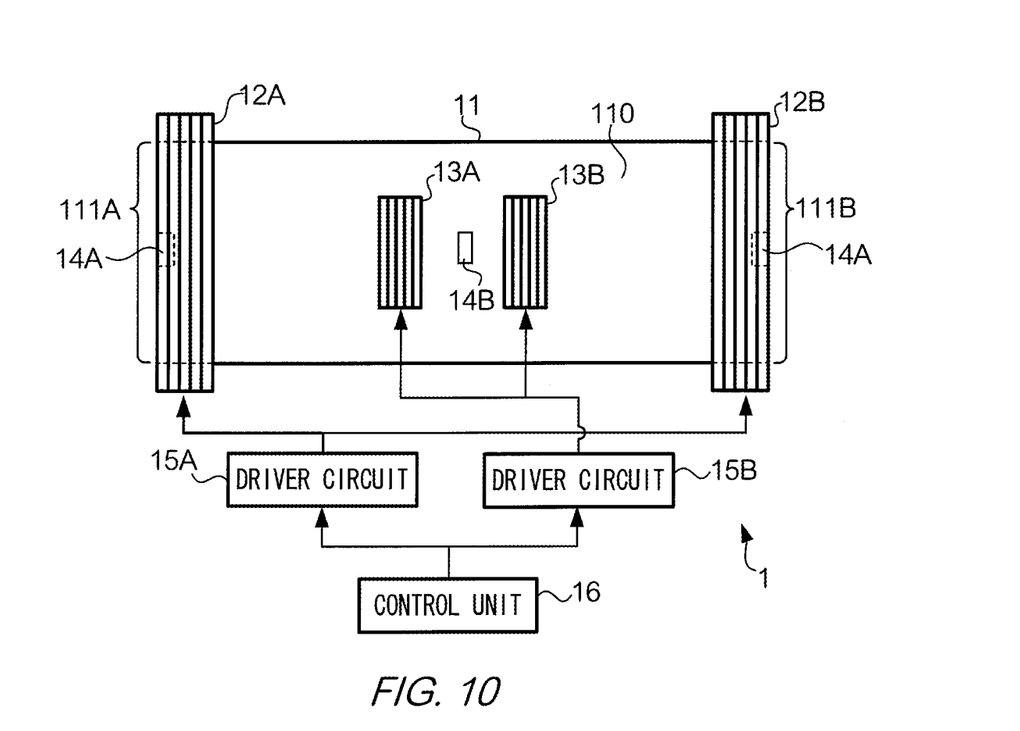
FIG. 10 shows an example of an external view of magnetic shielding device 1 according a second exemplary embodiment.

FIG. 10 shows an example of an external view of magnetic shielding device 1 according a second exemplary embodiment. Magnetic shielding device 1 includes passive shield 11, external coil 12, internal coil 13, magnetic sensor 14, driver circuit 15, and control unit 16. Magnetic shielding device 1 includes both the passive shield (passive shield 11) and the active shield (external coil 12 and internal coil 13). In magnetic shielding device 1, a magnetic field cancelled by external coil 12 is reduced by passive shield 11 and is further reduced by internal coil 13.

Passive shield 11 is made of conductive material having a high conductivity such as Aluminum. Passive shield 11 may be made of ferromagnetic substance, such as permalloy, ferrite, or amorphous of iron, chromium, or cobalt. Passive shield 11 has inner space 110 and at least one opening 111. Passive shield 11 has tubular shape whose cross section has square shape, with two openings 111. Inner space 110 is so large that the inner space can accommodate a magnetic field measuring device (for example, a magnetocardiographic device) and a tested body (for example, a person). External coil 12 is a coil to cancel a magnetic field near the opening 111. Internal coil 13 is a coil to cancel a magnetic field in inner space 110. Helmholtz coils (a set of two coils) are used as external coil 12 and internal coil 13, for example. Magnetic sensor 14 measures a magnetic field. A unique magnetic sensor 14 is used for each of external coil 12 and internal coil 13. In this example, magnetic sensor 14A corresponds to external coil 12 and magnetic sensor 14B corresponds to internal coil 13.

Figure 11:
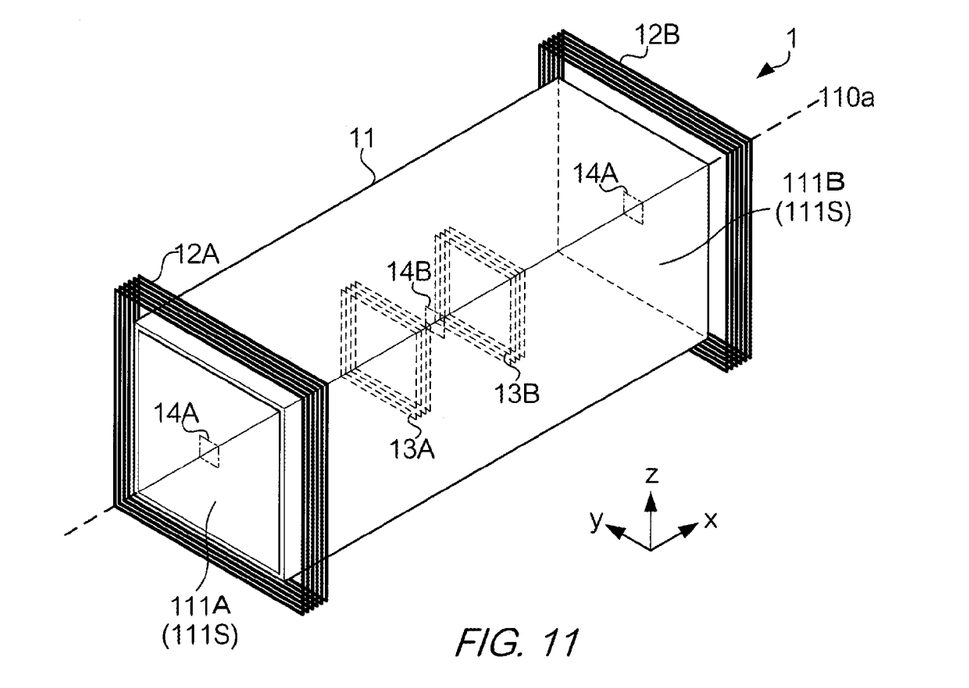
FIG. 11 shows an example of a configuration of magnetic shielding device 1.
Figure 12A:
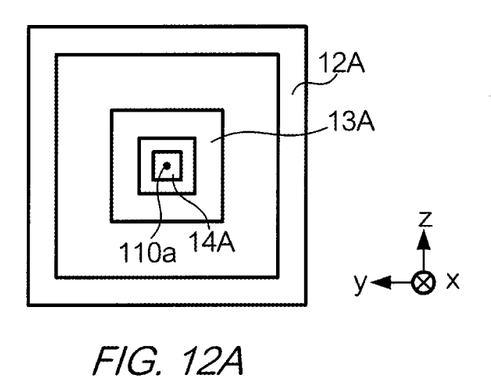
FIGS. 12A and 12B show an example of a spatial configuration (layout) of magnetic sensor 14.
Figure 12B:
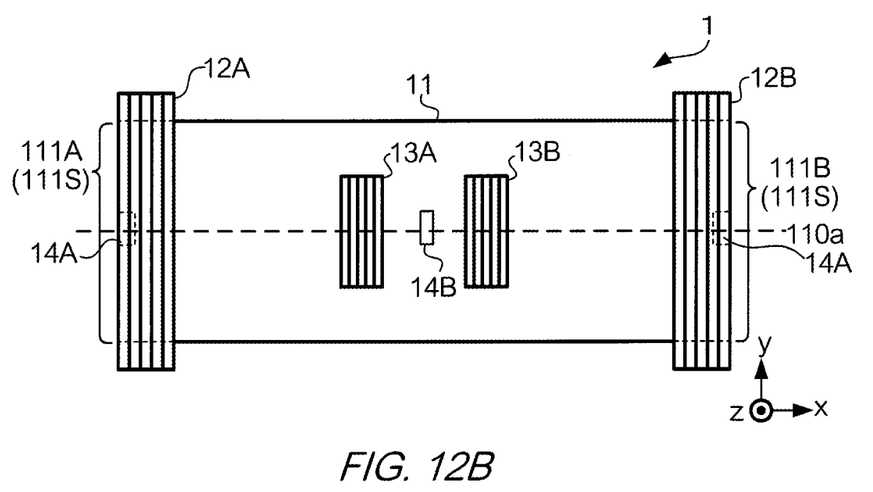

FIG. 11 shows an example of a configuration of magnetic shielding device 1. For the description below, a three dimensional orthogonal coordinate system is defined. In the coordinate system, x-axis, y-axis, and z-axis are defined as a direction along the width direction, the depth direction, and the height direction of passive shield 11, respectively. Passive shield 11 has two opening s 111A and 111B, at the end in a direction of x-axis. External coil 12A is installed near opening 111A, and external coil 12B is installed near opening 111B. These coils are wound around passive shield 11. In this example, the edge face of external coil 12A is identical with the edge face 111S of opening 111A. Further, the edge face of external coil 12B is identical with the edge face 111S of opening 111B. Internal coils 13A and 13B are located in inner space 110 so as to sandwich a target space (in this example, the target space includes the center of inner space 110) whose magnetic field it to be cancelled, FIGS. 12A and 12B show an example of a spatial configuration (layout) of magnetic sensor 14. FIG. 12A shows a view from a viewpoint on a positive x-axis. FIG. 12B shows a schematic cross section along x-y plane. Magnetic sensor 14A is located at the center (the center of gravity) of opening 111, for example. Magnetic sensor 14A measures x-component of a magnetic field near opening 111. Magnetic sensor 14B is located in the target space. Magnetic sensor 14B measures x-component of a magnetic field in the target space. It is to be noted that, in this example, resolution (in magnetic field) of magnetic sensor 14B is higher than that of magnetic sensor 14A.

Referring to FIG. 10 again. Driver circuit 15A is a circuit to drive external coil 12. Driver circuit 15B is a circuit to drive internal coil 13. Control unit 16 controls driver circuits 15A and 15B, in response to a magnetic field measured by magnetic sensor 14. Control unit 16 is a computer device including a CPU, a ROM, and a RAM.

Control unit 16 receives a signal showing results of the measurement (more specifically, showing a magnitude and direction of the magnetic field) of the magnetic field, from magnetic sensors 14A and 14B. Control unit 16 controls driver circuit 15A so that the magnitude of a magnetic field at edge face 111S is less than a predetermined threshold. Further, control unit 16 controls driver circuit 15B so that the magnitude of a magnetic field in inner space 110 is less than a predetermined threshold.

Driver circuit 15A provides current to drive external coil 12 so that a magnetic field at edge face 111S is cancelled. Here, to "cancel" a magnetic field means to control a magnetic field so that the magnetic field is within a predetermined range including zero. The predetermined range is determined based on the resolution of magnetic sensor 14A in a magnetic field. The predetermined range is, for example, less than or equal to 1 pT (pico tesla). Driver circuit 15A provides to coils 12A and 12B, current having the same direction and the same magnitude. By providing current, the magnitude of the x-components of the magnetic field in inner space 110 is reduced compared with a case where no external coil is used, another case where the magnetic field at the center of the inner space is cancelled, or still another case where external coil 12 generates a magnetic field having the same magnitude and the opposite direction with the external magnetic field.

Driver circuit 15B provides current to drive internal coil 13 so that a magnetic field in the inner space 110 is cancelled. As described above, to "cancel" a magnetic field means to control a magnetic field so that the magnetic field is within a predetermined range including zero. Here, the predetermined range is determined based on the resolution of magnetic sensor 14B in a magnetic field. The predetermined range is, for example, less than or equal to 1 pT (pico tesla). Driver circuit 15B provides to coils 13A and 13B, current having the same direction and the same magnitude. By providing current, the magnitude of the x-components of the magnetic field in inner space 110 is reduced compared with a case where no internal coil is used.

It is to be noted that, in this case, the dynamic range of a magnetic field generated by external coil 12 is greater than the dynamic range of a magnetic field generated by internal coil 13. Further, the resolution (in a generated magnetic field) of internal coil is greater than that of external coil 12.

Figure 13:
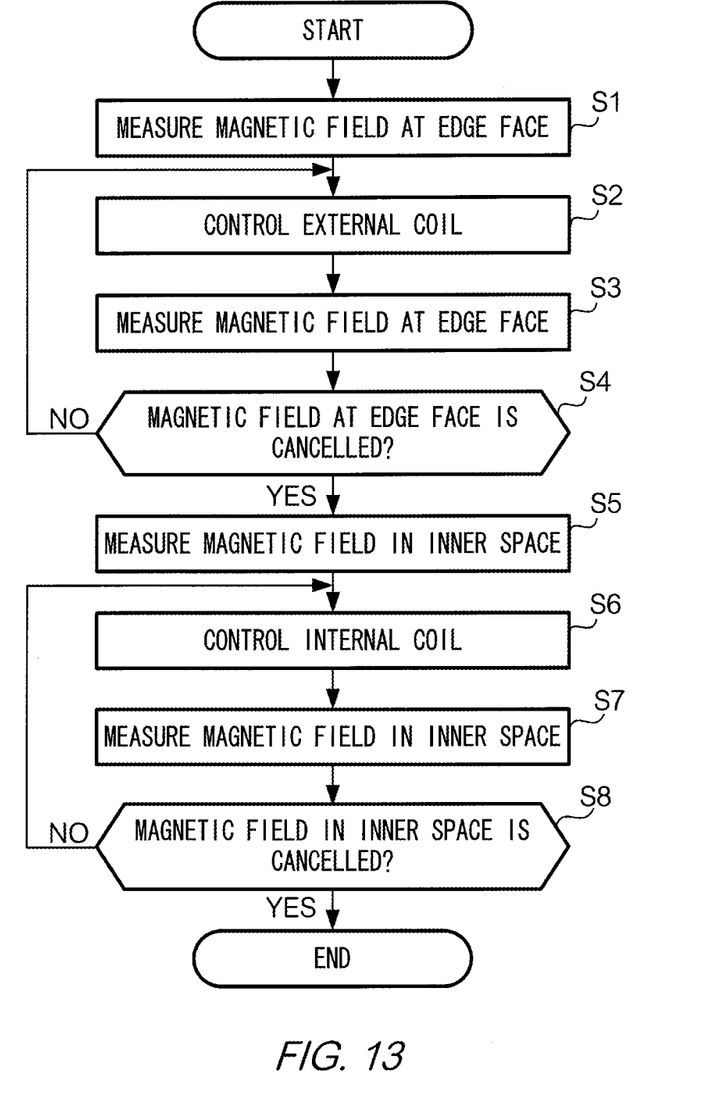
FIG. 13 shows an example of a flowchart illustrating an operation of magnetic shielding device 1.

FIG. 13 shows an example of a flowchart illustrating an operation of magnetic shielding device 1. The following operation is triggered by activating magnetic shielding device 1, for example.

In step S1, control unit measures a magnetic field at edge face 111S. More specifically, control unit 16 obtains a signal showing a measured magnetic field (a magnitude and a direction of the magnetic field).

In step S2, control unit 16 controls driver circuit 15A to provide current to external coil 12. More specifically, control unit 16 outputs a signal causing driver circuit 15A to provide to external coil 12 current to generate a magnetic field canceling a magnetic field measured by magnetic sensor 14A. Driver circuit 15A provides current to external coil 12 according to the signal output from control unit 16. The current has a direction by which a magnetic field opposite to a magnetic field measured by magnetic sensor 14A is generated. The current has a magnitude by which a magnetic field having the same magnitude as a magnetic field measured by magnetic sensor 14A is generated. The relationship between the magnitude of current provided to external coil 12 and a magnetic field generated by external coil 12 is stored in the ROM, for example.

In step S3, control unit 16 measures a magnetic field at edge face 111S.

In step S4, control unit determines whether the magnitude of the measured magnetic field at edge face 111S is cancelled. If it is determined that the magnitude of the measured magnetic field is cancelled (step S4: YES), control unit 16 transfers the operation to step S5. If it is not determined that the magnitude of the measured magnetic field is cancelled (step S4: NO), control unit 16 transfers the operation to step S2 again.

In step S5, control unit 16 measures a magnetic field in inner space 110. More specifically, control unit 16 receives a signal from magnetic sensor 14B showing the measured magnetic field.

In step S6, control unit 16 controls driver circuit 15B to provide current to internal coil 13. More specifically, control unit 16 outputs a signal causing driver circuit 15B to provide to internal coil 13 current to generate a magnetic field canceling a magnetic field measured by magnetic sensor 14B. Driver circuit 15B provides current to internal coil 13 according to the signal output from control unit 16. The current has a direction by which a magnetic field opposite to a magnetic field measured by magnetic sensor 14B is generated. The current has a magnitude by which a magnetic field having the same magnitude as a magnetic field measured by magnetic sensor 14B is generated. The relationship between the magnitude of current provided to internal coil 13 and a magnetic field generated by internal coil 13 is stored in the ROM, for example.

In step S7, control unit 16 measures the magnetic field in inner space 110 again.

In step S8, control unit determines whether the magnitude of the measured magnetic field in inner space 110 is cancelled. If it is determined that the magnitude of the measured magnetic field is cancelled (step S8: YES), control unit 16 terminates the operation shown in FIG. 13. If it is not determined that the magnitude of the measured magnetic field is cancelled (step S8: NO), control unit 16 transfers the operation to step S6 again.

According to processes in steps S1 to S4, the magnetic field in inner space 110 decreased near zero, with an order of the resolution of external coil 12, According to processes in steps S5 to S8, the magnetic field in inner space 110 decreased near zero, with an order of the resolution of internal coil 12. According to the present exemplary embodiment, the external magnetic field is more effectively cancelled compared with a case with external coil 12 alone or a case with internal coil 13 alone.

The invention is not restricted to the embodiment described above. Various modifications may be applied to the embodiment. Some modifications will be described in the following. Two or more modification may be combined.

The coils of the shielding device are not restricted to the above described example. The shielding device may have a coil to control a gradient of a magnetic field in the target space, in addition to or instead of the above described coils.

Figure 14:
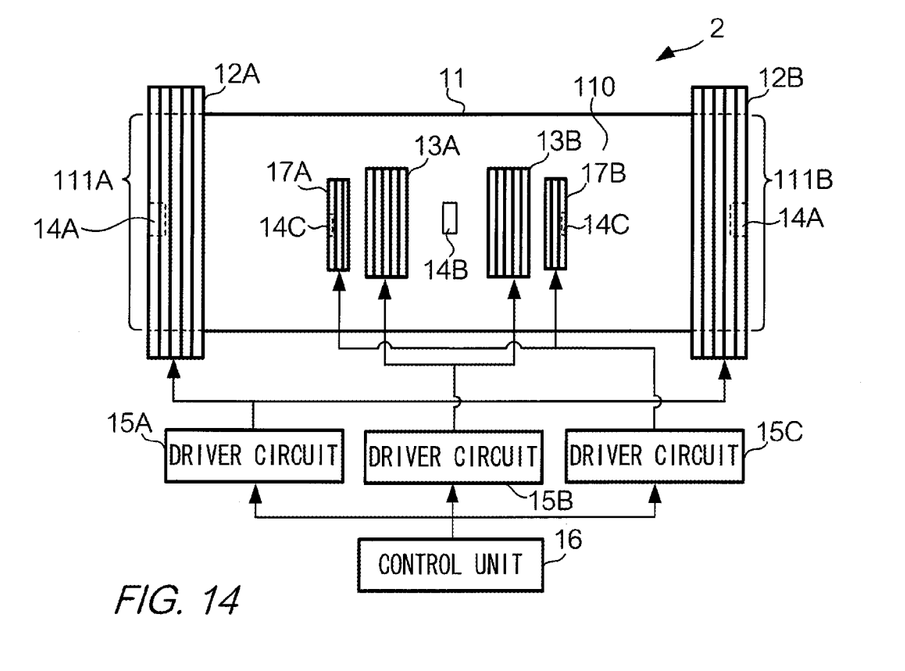
FIG. 14 shows an example of an external view of magnetic shielding device 2 according a modification of the second exemplary embodiment.

FIG. 14 shows an example of an external view of magnetic shielding device 2 according a modification of the second exemplary embodiment. Magnetic shielding device 2 includes gradient coil 17, magnetic sensor 14C, and a circuit 15C. Description for elements common with magnetic field shield device 1 is omitted. Gradient coil 17 is a coil to control a gradient of magnetic field in inner space 110. For example, two coils 17A and 17B are used. Magnetic sensor 14C is a sensor corresponding to gradient coil 17. Magnetic sensor 14C is located at a face where gradient coil 17 is located, for example. Magnetic sensor 14C measures x-component of the magnetic field at the face where gradient coil 17 is located. Driver circuit 15C is a circuit to drive gradient coil 17.

In this modification, control unit 16 receives a signal showing the measured magnetic field, from magnetic sensor 14C. Control unit 16 calculates a gradient of the magnetic field based on the magnetic field measured by magnetic sensor 14C. Control unit 16 controls driver circuit 15C so that the gradient of the magnetic field is cancelled. Driver circuit 15C provides current to drive gradient coil 17 according to a signal output from control unit 16. Here, to "cancel" a gradient of a magnetic field means controlling the gradient to be within a predetermined range including zero. The predetermined range relates to a range to be considered as that the magnetic field is constant (or uniform). Driver circuit 15C provides current having opposite directions, to coils 17A and 17B. By controlling current provided to coils 17A and 17B, the gradient of the magnetic field in the inner space between coils 17A and 17B is reduced, compared with a case where gradient coil 17 is not used.

Figure 15:
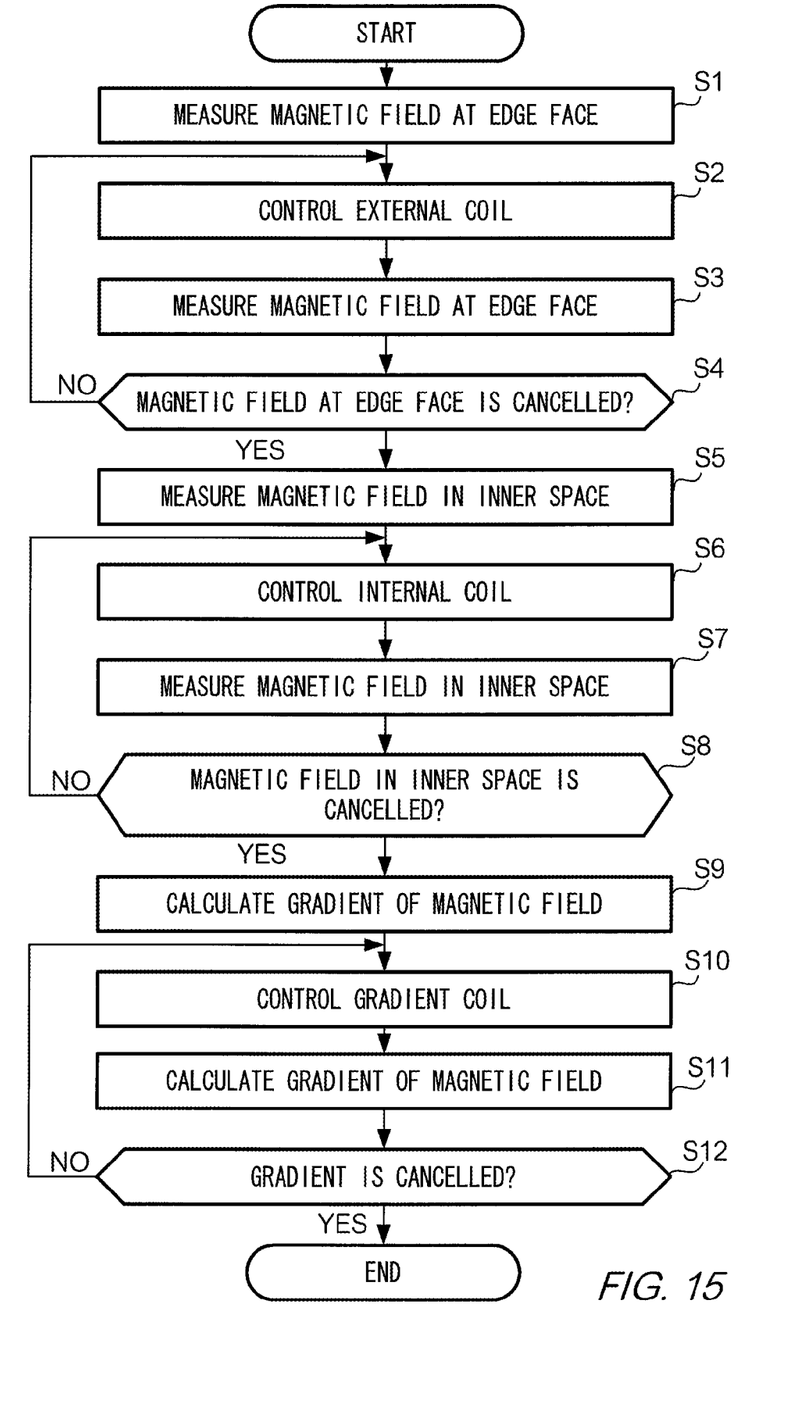
FIG. 15 shows an example of a flowchart illustrating an operation of magnetic shielding device 2.

FIG. 15 shows an example of a flowchart illustrating an operation of magnetic shielding device 2. In magnetic shielding device 2, steps S9 to S12 are further executed in addition to steps S1 to S8 shown in FIG. 13.

In step S9, control unit 16 calculates a gradient of the magnetic field in inner space 110. More specifically, control unit 16 receives a signal showing the magnetic field measured by magnetic sensor C, and calculates the gradient A according to the following equation (3).

$$A = H_{max} - H_{min} \quad (3)$$

Here, Hmax and Hmin denote the maximum and the minimum magnetic field measured by magnetic sensor 14C.

In step S10, control unit 16 controls driver circuit 15C to provide current to gradient coil 18, as well as measuring magnetic fields H1 and H2 generated by gradient coils 17A and 17B, respectively. Control unit 16 controls driver circuit 15C so that the measured magnetic fields satisfy the following equation (4).

$$\alpha = |H_1 - H_2| - (H_{max} - H_{min}) = 0 \quad (4)$$

More specifically, control unit 16 outputs a signal causing driver circuit 15C to provide current so that the gradient of the magnetic field is cancelled. Driver circuit 15C provides current to a gradient coil 17 according to the signal output from control unit 16.

In step S11, control unit 16 calculates the gradient of the magnetic field in inner space 110 again.

In step S12, control unit 16 determines whether the gradient of the magnetic field in inner space is cancelled. If it is determined that the gradient is cancelled (step S12: YES), control unit 16 terminates the operation. If it is not determined that the gradient is not cancelled (step S12: NO), control unit 16 transfers the operation to step S10 again. According to processes in steps S9 to S12, the gradient of the magnetic field in inner space 110 become near zero.

It is to be noted that magnetic sensor 14C may be omitted in a case that gradient coil 17 is used. In such a case, control unit 16 may control gradient coil 18 based on a signal from magnetic sensor 14B.

The cross section perpendicular to x-axis is not restricted to a square. For example, the cross section perpendicular to x-axis may be a polygon other than a square, a circle, or an ellipse. Passive shield may not have two openings 111 at the edges. At least one opening may be covered by a cover. Further, passive shield 11 may be made of multi-layered material.

The shape of external coil 12, internal coil 13, and gradient coil 17 is not restricted to the example shown in the above exemplary embodiments. The shape may be a polygon other than a square, a circle, or an ellipse.

Each of external coil 12, internal coil 13, and gradient coil 17 is not restricted to a Helmholtz coil. A single coil may be used external coil 12 and internal coil 13.

In the above embodiment, only an x-axis component of the magnetic field is cancelled. However, two or more axes components may be cancelled or controlled. In such a case, magnetic shielding device 1 has two or more sets of internal coils 13. For example, magnetic shielding device 1 may have three sets of internal coils 13, for x-, y-, and z-axes. Each component of the magnetic field may be cancelled or controlled.

The number of magnetic sensor 14 and the layout thereof are not restricted to examples shown in the above exemplary embodiments. For example, magnetic sensor 14A may be located at the center of gravity of one of opening 111A and 111B.

A method for controlling a coil is not restricted to the example described above. In the above embodiment, each coil is feedback controlled. A coil may be controlled by a method other than the feedback control.

C. Third Exemplary Embodiment

The first exemplary embodiment and the second exemplary embodiment may be combined. For example, gradient coil 17 may be used in addition to or instead of internal coil 13 in the first exemplary embodiment.

What is claimed is:
1. A magnetic shielding device, comprising:
   a passive shield housing having an inner space and first and second openings, the passive shield housing extending in a first direction, the first and second openings being located at two ends of the Passive shield housing in the first direction;
   a first coil that is provided around the first opening in which a first magnetic field exists;
   a second coil that is provided around the second opening in which a second magnetic field exists;
   a third coil that is provided inside of the inner space between the first and second coils;
   a driving circuit that applies a first current to the first and second coils to respectively cancel the first and second magnetic fields and that applies a second current to the third coil;
   a first magnetic sensor that measures the first magnetic field so as to output a first value corresponding to the first magnetic field;
   a second magnetic sensor located at inside of the inner space between the first and second openings so that the second magnetic sensor is closer to a center of the inner space than the first magnetic sensor, the second magnetic sensor outputting a second value corresponding a third magnetic field; and a controller that is configured to calculate a magnetic field gradient between the first and second magnetic sensors based on the first and second values and a distance between the first and second magnetic sensors in the first direction, wherein when the controller determines that the magnetic field gradient is equal to or less than a predetermined value, the controller applies the first current to the first and second coils and the second current to the third coil, and when the controller determines that the magnetic field gradient is more than the predetermined value, the controller changes one of the first current and the second current to a different current.

2. The magnetic shielding device according to claim 1, wherein the inner space has a correction target space therein, a magnetic field in the correction target space is corrected by the first coil, and the second magnetic sensor is located closer to the correction target space than the first magnetic sensor.

3. The magnetic shielding device according to claim 2, wherein the predetermined value is determined based on a magnetic field measurement use range of a magnetic field measuring device located in the correction target space.

4. The magnetic shielding device according to claim 1, wherein the predetermined value is equal to or less than 10 nT.

5. The magnetic shielding device according to claim 1, wherein the first magnetic sensor is located at the first opening.

6. The magnetic shielding device according to claim 5, wherein the first magnetic sensor is located at a center of the first opening.

7. The magnetic shielding device according to claim 1, wherein a first dynamic range, which is a first magnitude of the first magnetic field generated by the first coil, is greater than a second dynamic range, which is a second magnitude of the second magnetic field generated by the second coil.

8. The magnetic shielding device according to claim 1, wherein a resolution of the second coil which corresponds to how precisely the second coil controls the second magnetic field is higher than a resolution of the first coil which corresponds to how precisely the first coil controls the first magnetic field.

9. A method for controlling a magnetic shielding device, the magnetic shielding device including:

a passive shield housing having an inner space and first and second openings, the passive shield housing extending in a first direction, the first and second openings being located at two ends of the passive shield housing in the first direction;

a first coil that is provided around the first opening in which a first magnetic field exists;

a second coil that is provided around the second opening in which a second magnetic field exists;

a third coil that is provided inside of the inner space between the first and second coils;

a first magnetic sensor that measures the first magnetic field so as to output a first value corresponding to the first magnetic field; and a second magnetic sensor located at inside of the inner space between the first and second openings so that the second magnetic sensor is closer to a center of the inner space than the first magnetic sensor, the second magnetic sensor outputting a second value corresponding a third magnetic field, the method comprising:

applying a first current to the first and second coils to respectively cancel the first and second magnetic fields, applying a second current to the third coil, and calculating a magnetic field gradient between the first and second magnetic sensors based on the first and second values and a distance between the first and second magnetic sensors in the first direction, wherein when the magnetic field gradient is equal to or less than a predetermined value, the first current is applied to the first and second coils and the second current is applied to the third coil, and when the magnetic field gradient is more than the predetermined value, one of the first current and the second current is changed to a different current.

* * * * *